United States Patent [19]

Kano et al.

[11] Patent Number: 5,188,968

[45] Date of Patent: Feb. 23, 1993

[54] METHOD AND REACTION KIT FOR AGGLUTINATION DETECTION

[75] Inventors: Tokio Kano, Nesconset, N.Y.; Toshinobu Niimura, Hachioji, Japan; Hiroyuki Yonekawa, St. James, N.Y.

[73] Assignee: Olympus Optical Co., Ltd., Tokyo, Japan

[21] Appl. No.: 841,769

[22] Filed: Mar. 2, 1992

Related U.S. Application Data

[63] Continuation of Ser. No. 458,143, Dec. 28, 1989, abandoned.

[51] Int. Cl.$^5$ ............................................. G01N 33/53
[52] U.S. Cl. ........................................ 436/501; 422/58; 422/61; 422/73; 422/102; 436/165; 436/520; 436/539
[58] Field of Search ................ 422/58, 61, 73, 102; 436/165, 501, 520, 533, 539, 541; 424/11

[56] References Cited

U.S. PATENT DOCUMENTS

| | | | |
|---|---|---|---|
| 4,303,616 | 12/1981 | Kano et al. | 422/102 |
| 4,436,827 | 3/1984 | Tamagawa | 436/534 |
| 4,591,570 | 5/1986 | Chang | . |
| 4,596,695 | 6/1986 | Cottingham | 422/58 |
| 4,756,884 | 7/1988 | Hillman et al. | 422/73 |
| 5,066,465 | 11/1991 | Kano et al. | 422/58 |

FOREIGN PATENT DOCUMENTS

| | | |
|---|---|---|
| A1-0034049 | 8/1981 | European Pat. Off. . |
| A2-0057110 | 8/1982 | European Pat. Off. . |
| A2-0321736 | 6/1989 | European Pat. Off. . |
| 3438245A1 | 5/1985 | Fed. Rep. of Germany . |
| 56-2559 | 1/1981 | Japan . |
| 61-39321 | 1/1986 | Japan . |
| 61-44268 | 10/1986 | Japan . |

*Primary Examiner*—Robert J. Hill, Jr.
*Attorney, Agent, or Firm*—Frishauf, Holtz, Goodman & Woodward

[57] ABSTRACT

A reaction kit is provided with a reaction zone of suitable cross-sectional area to aspirate a sample by capillarity and a transparent plate with a flat surface in at least part of the reaction zone, and a supporting base to incline the reaction zone at a specified angle. The reaction zone is normally a space formed by two opposite transparent plates and spacers inserted between these two transparent plates. A supporting base may be molded separately, the transparent plates and spacers being set on the base at the time of measurement, or alternatively the base may be molded integrally with at least one of the plates defining the reaction zone. Further, substances with specificity such as antigens or antibodies may be coated on a surface in the reaction zone. The occurrence or non-occurrence of an agglutination reaction may be determined by introducing a particle suspension containing particles with specific bonding properties and a substance with specific bonding properties into the reaction zone by means of capillarity, leaving the apparatus for a predetermined time to carry out the reaction, and thereafter observing the particle distribution pattern.

13 Claims, 5 Drawing Sheets

METHOD AND REACTION KIT FOR AGGLUTINATION DETECTION

This application is a continuation of application Ser. No. 07/458,143, filed Dec. 28, 1989, now abandoned.

BACKGROUND OF THE INVENTION

1. Field of the Invention

This invention concerns a reaction kit for carrying out agglutination reactions, and in particular, a reaction kit used for hemanalysis involving immunological antigen-antibody reactions.

2. Description of the Related Art

Conventional reaction vessels used for detections by using immunological agglutination reactions are, for example, of the type disclosed in U.S. Pat. No. 4,303,616. These reaction vessels are usually referred to by the generic name of microplates.

One detection method using this kind of reaction vessel is a is particle agglutination method whereby antigens or antibodies in the sample are detected based on an immunological agglutination reaction. In this method, a specific marker particle is used and antigens or antibodies which conjugate specifically to the substance being measured are coated on the surface of the particle. To detect viruses in blood, for example, a man-made marker particle on which the antibodies against the virus are coated is used. The method is carried out using said reaction vessel as follows. First, said marker particles are mixed with the sample in the reaction vessel, an immunological reaction takes place with the antigens or antibodies in the sample, and the marker particles collect on one of the walls (for example the bottom) of the reaction vessel. The particles collected on the wall of the vessel however have a different distribution pattern depending on whether there was or was not an immunological reaction with the substance being measured in the sample. It is therefore possible to determine a positive or negative reaction for the substance from the distribution pattern of marker particles on the wall of the vessel.

Another method, the mixed agglutination method, was reported by A. S. Wiener and M. H. Herman. This method was subsequently improved in stages so that it could even determine blood group. To determine blood group, for example, the following procedure is carried out using said reaction vessel. First, suitable quantities of a fixed concentration of red blood cells and a fixed dilution of serum are mixed in the reaction vessel, and allowed to stand for a certain time. As in the method described above, the distribution pattern of sedimented red blood cells is different according to whether there was or was not an immunological reaction between antigens on the red blood cells, and antibodies in the serum. It is therefore possible to determine a positive or negative reaction from the distribution pattern of sedimented red blood cells.

The distribution pattern obtained by these methods can be easily observed with the naked eye, but it may also be analyzed automatically by the methods disclosed in Unexamined Published Japanese Patent Application No. 54-78499. Further, in Examined Japanese Utility Model No. 61-39321, a method is disclosed whereby a particle agglutination pattern is formed on an optically flat focus plane, and the agglutination image is easily observed.

In the reaction vessel described in U.S. Pat. No. 4,303,616, however, at least about 50 $\mu l$ of liquid is required to form a stable and accurate distribution pattern. If the quantity of liquid is less than 50 $\mu l$, the sedimentation of particles is disturbed and to be irregular due to surface tension, and the distribution pattern does not form correctly. For this reason, the depth of reaction solution in this reaction vessel requires no less than 3 mm. It is moreover for this reason that the distribution pattern takes a long time to form. In other words, the particles such as red blood cells which form the distribution pattern have to move over a considerable distance, and as a result, the time required to form the pattern is long.

The above problem, namely that the distribution pattern is not formed correctly when the quantity of liquid is too small, can be overcome to some extent by making the internal diameter of the reaction vessel smaller. In this case, however, the surface tension between the reaction solution and the walls of the reaction vessel comes into play, and the liquid surface again sinks or rises irregularly. The result is that it becomes difficult to accurately observe the distribution pattern which is formed.

Further, if the internal diameter of the vessel is made smaller so that the quantity of liquid become smaller, the time required to form the distribution pattern is shorter, but the problem then arises that it is necessary to handle minute quantities of reagent. In particular, when the quantity of liquid is no greater than 5 $\mu l$, it becomes extremely difficult technically to pipette reagents accurately with high reproducibility.

Further, very fine surface working is required to manufacture vessels of small internal diameter precisely, for example recesses with a diameter of the order of several hundred micrometers, and it is also difficult to manufacture them efficiently.

The method described in Examined Japanese Utility Model No. 61-39321, on the other hand, is a flow type measurement method which uses a rolling pump to introduce a particle suspension into the reaction vessel. The number of samples or items which can be measured simultaneously by such a flow type method is however limited, and it is impossible to simultaneously handle many samples over multiple items as in the method in which a conventional microplate is used. Further, there is a large error in introducing measured quantities of a sample by a rolling pump, and the method is not suited to the analysis of minute quantities of samples of the order of $\mu m$.

SUMMARY OF THE INVENTION

This invention aims to provide a reaction kit for agglutination reactions, wherein an accurate distribution pattern of sedimented particles is formed in a short time, and the distribution pattern obtained can be observed accurately.

Said objectives are achieved by a kit comprising a reaction zone defining means for defining a reaction zone suitable for aspirating the sample into the interior of the reaction zone by capillarity, the reaction zone defining means including a transparent plate with a flat surface in at least part of said reaction zone, and a supporting base to incline said reaction zone at a specified angle.

The reaction zone is generally a space formed by 2 transparent plates with flat surfaces, and 2 spacers inserted between these 2 plates at a specified distance from each other.

The supporting base inclines the reaction zone at a specified angle and maintains the angle. The reaction zone defining means is mounted on the base such that one of the sides into which a spacer has been inserted is in the lower position.

In the reaction kit of this invention, the sample is introduced by means of capillarity into the reaction zone from an opening of the reaction zone. The cross-sectional area of the reaction zone is therefore suitable for asp rating the sample into the interior of the reaction zone by capillarity. This cross-sectional area varies according to the sample being observed, but if the sample consists of blood components, it is preferably 0.2–5 mm$^2$.

DETAILED DESCRIPTION OF THE PREFERRED EMBODIMENTS

As described above, in the reaction kit according to this invention, the reaction zone is defined enclosed by two plates and spacers which maintain these plates at a small separation apart. Also, to carry out the reaction, the sample is filled in the reaction zone. The liquid surface of the sample in the reaction zone is therefore constantly in contact with the inner wall of the zone, and is maintained flat. For this reason, there is no disturbance of the particle distribution pattern. In addition, the cross-sectional area of the reaction zone is such that the sample can be introduced into the reaction zone by capillarity, and is extremely small. For this reason, the distance over which the sedimented particles move is much shorter, and the distribution pattern can be formed in a short time.

Further, the sample is introduced by means of capillarity, and may for example be dropped into the opening of the reaction zone. The quantity of sample solution in the reaction zone is always constant regardless of the quantity dropped in, and it is not therefore particularly essential to pipette small quantities accurately.

We shall now describe some embodiments of the reaction kit according to this invention with reference to the drawings.

Figure 1A:
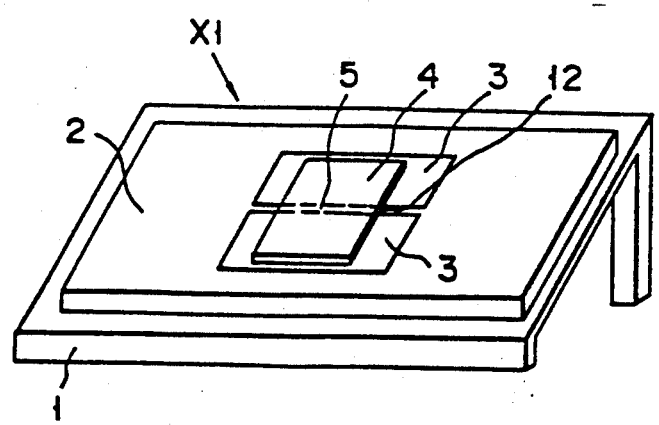
Fig 1A is a perspective view showing one embodiment of the reaction kit according to this invention.
Figure 1B:
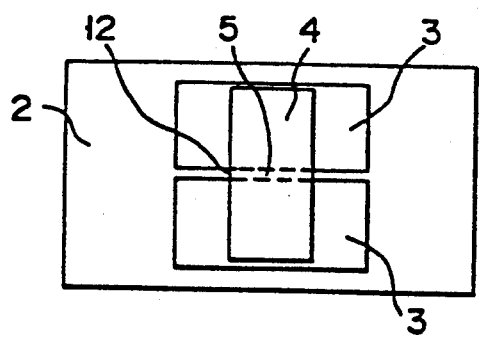
FIG. 1B is a plan view seen from direction X1 of a part of the kit shown in FIG. 1A.
Figure 1C:
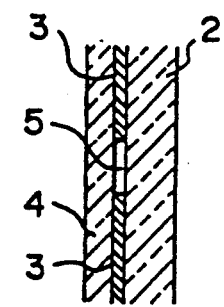
FIG. 1C is a cross-sectional view of the part of the kit shown in FIG. 1B.

FIG. 1A is a perspective view of the reaction kit of this invention; FIG. 1B is a plan view seen from direction X1 of the reaction zone defining means shown in FIG. 1A; and FIG. 1C is a sectional view of the portion of the reaction kit shown in FIG. 1B. As shown in these figures, in the reaction zone is defined by a lower plate 2 and an upper plate 4 which preferably consist of transparent members, and which are arranged substantially parallel to each other on either side of two spacers 3. The area 5 enclosed by lower plate 2, upper plate 4 and the two spacers is the reaction zone where agglutination reactions are carried out, and it is also a sample inlet channel for introducing the sample. The two sides where spacers 3 are not inserted constitute a sample inlet port 12 from which the sample is injected or exhausted. A supporting base 1 is provided with an inclined surface at a specified angle with respect to the horizontal. The reaction zone defining means (the two plates 2, 4 and two spaces 3) is mounted on the inclined surface of this supporting base.

In this kit, it is desirable that the thickness of spacers 3, that is the distance between lower plate 2 and upper plate 4, is 0.05–1.0 mm, and that the distance between the two spacers 3 is 0.1–1.0 mm. Further, it is desirable that the length of the long direction of reaction zone 5, that is the width of upper plate 4, is 3–10 mm. It is moreover desirable that the slope of the inclined surface of the supporting base 1 is 10°–60° with respect to the horizontal.

This reaction vessel kit may be used in tests to verify the occurrence or non-occurrence of agglutination reactions. In the case where, for example, this kit is used to establish the occurrence of a reaction between blood corpuscles and antibodies in serum, the following procedure is carried out.

Figure 2A:
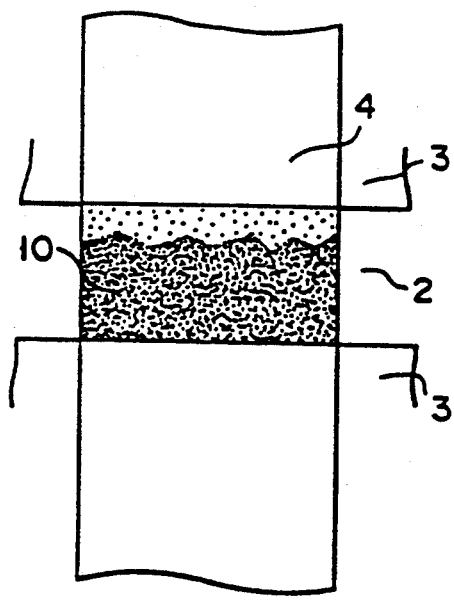
FIG. 2A shows a sediment particle distribution pattern obtained when there was an agglutination reaction in an agglutination test carried out using the reaction vessel kit shown in FIGS. 1A–1C.
Figure 2B:
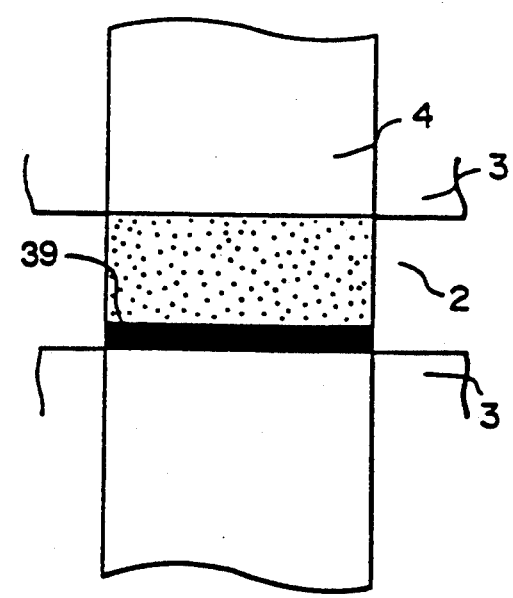
FIG. 2B shows a sediment particle distribution pattern obtained when there was no agglutination reaction in an agglutination test carried out using the reaction kit shown in FIGS. 1A–1C.
Figure 3A:
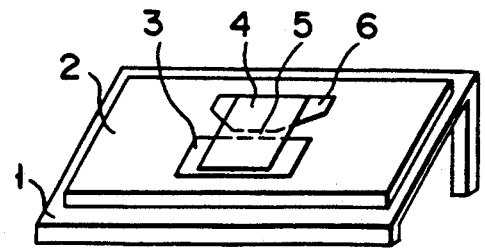
FIG. 3A is a perspective view of a modification with a different shape of spacer.
Figure 3B:
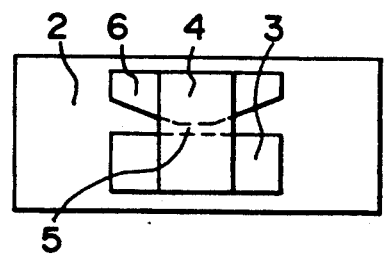
FIG. 3B is a plan view of a part of the kit shown in FIG. 3A
Figure 4A:
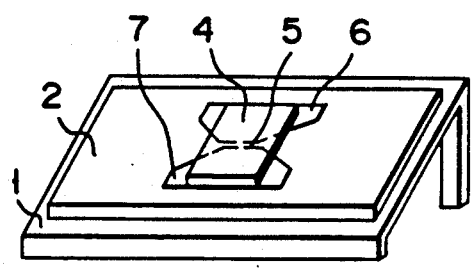
FIG. 4A is a perspective view of another modification with a different shape of spacer.
Figure 4B:
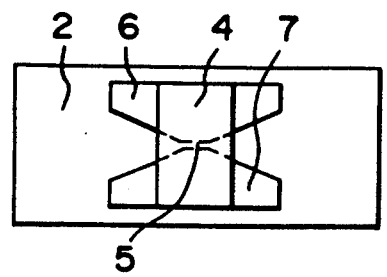
FIG. 4B is a plan view of a part of the kit shown in FIG. 4A.

First, a fixed concentration of a blood corpuscles suspension and a fixed dilution of serum are mixed in a test tube. The mixture is then aspirated by a pipette, and a suitable quantity is dropped to sample inlet port 12 of the reaction zone. The mixture dropped spreads by capillarity throughout the reaction zone 5. The kit is allowed to stand undisturbed for a certain time, and blood corpuscles sediment out. Since the reaction zone is inclined, the sedimented corpuscles move downwards along inclined lower plate 2 without collecting on lower plate 2. From the blood corpuscles distribution pattern formed in the lower part of the reaction zone, it is then possible to verify the occurrence or non-occurrence of a reaction. If the corpuscles agglutinated due to an antigen-antibody reaction, a positive pattern 10 is formed wherein the corpuscles ar spread uniformly to the upper part of inclined lower plate 2 as shown in FIG. 2A. On the other hand if there was no reaction and the corpuscles did not agglutinate, all the corpuscles move down inclined lower plate 2, and a negative pattern 39 is formed wherein the corpuscles are gathered in a line on the lowermost part of the reaction zone, as shown in FIG. 2B.

In the reaction kit shown in FIGS. 1A-1C, the spacers 3 are rectangular. The spacers need not however be rectangular, and may also be of the form of spacers 6 and 7 shown in FIGS. 3A-4B. By using spacers of such a form the sample inlet port is enlarged, and introduction of aliquot parts of sample is easier.

Figure 5A:
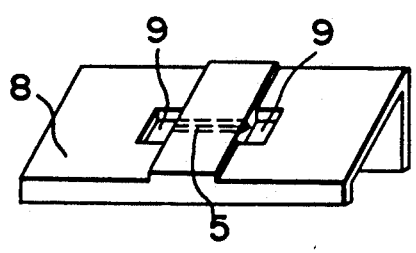
FIG. 5A is a perspective view of a modification wherein the part of the kit defining the reaction zone is integrally formed with the supporting base.
Figure 5B:
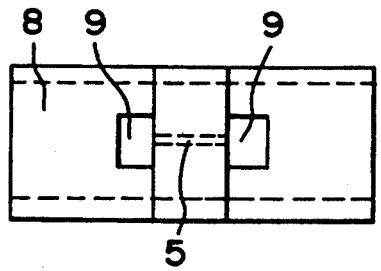
FIG. 5B is a plan view of the kit shown in FIG. 5A.

In the reaction vessel kit of this invention, the reaction zone defining means and the supporting base may be integrally molded. FIG. 5A and 5B show an integrated reaction kit of this type. As shown in these figures, a tubular reaction zone 5 of such a cross-sectional area as to permit aspiration of the sample by capillarity, is provided on the inclined surface 8, and sunken liquid troughs 9 are provided on both side edges of reaction zone 5.

Figure 6A:
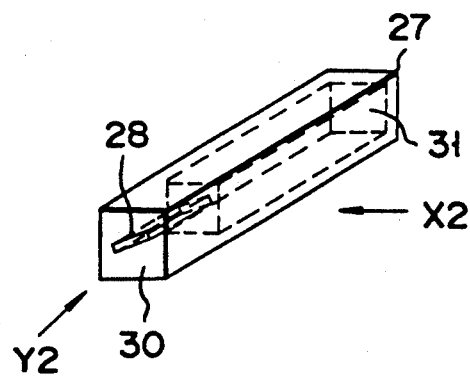
FIG. 6A is a perspective view showing another modification wherein the part of the kit defining the reaction zone is integrally formed with the supporting base.
Figures 6B, 6C:
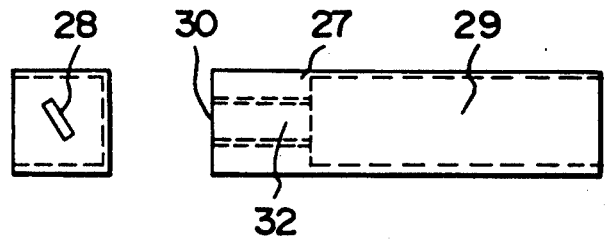
FIG. 6B is a plan view seen from direction Y2 of the kit shown in FIG. 6A.
FIG. 6C is a plan view seen from direction X2 of the kit shown in FIG. 6A.

The integrated reaction kit may also be molded in a rod shape. In the rectangular rod-shaped reaction kit 27 shown in FIGS. 6A-6C, there are provided a reaction zone 32 which is a throughhole having a specified angle with respect to the horizontal and a hollow 29 connected to this reaction zone 32. Reaction zone 32 has a cross-sectional area such that the sample can be aspirated by capillarity. In the case where this rod-shape reaction kit is used in agglutination reaction tests, the following procedure is carried out. First, the end 30 of rod-shaped member 27 is dipped in a previously prepared particle suspension, and the particle suspension is thereby introduced into reaction zone 32 from sample inlet port 28 by means of capillarity. After the suspension has been introduced into the reaction zone, member 27 is removed from the suspension, and laid horizontally to allow the reaction to proceed undisturbed for 10 min. After the reaction, by observing the particle distribution pattern formed in reaction zone 32, it is possible to determine whether there was or was not an agglutination reaction. In this rod-shaped reaction kit, reaction zone 32 is connected to hollow 29 and hollow 29 is connected to the outside via opening 31, so unnecessary pressure does not act on reaction zone 32. Further, by applying a negative pressure from opening 31, sample or wash solution may be forcibly aspirated. Reaction zone 32 may also be washed by introducing wash solution from opening 31, or simply by applying a positive pressure to opening 31.

We shall now describe some agglutination tests using the reaction kit according to this invention.

EXAMPLE 1

Determination of Human ABO Blood Group

Figure 8:
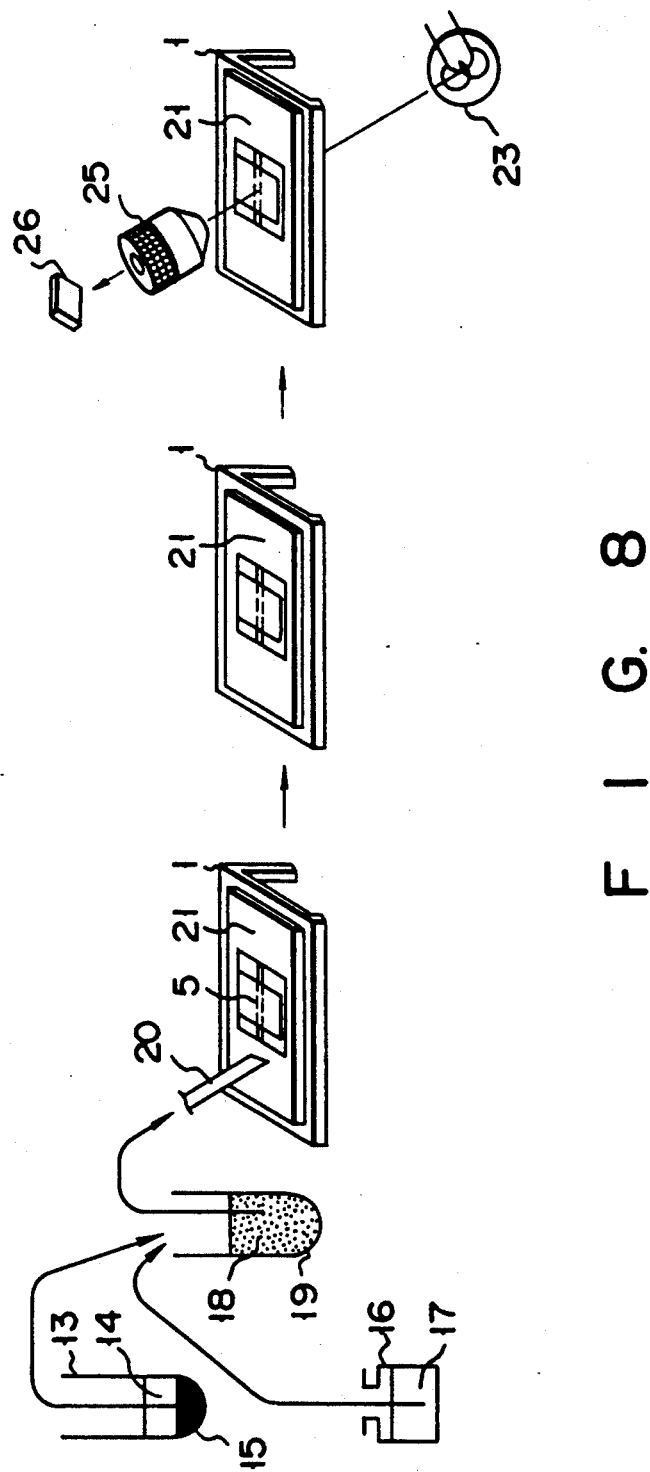
FIG. 8 is a view showing a process in an agglutination test using the reaction kit shown in FIGS. 1A–1C.

We shall describe the determination of human ABO blood group using the reaction kit of FIGS. 1A-1C with reference to FIG. 8.

First, a sample of blood is separated in test tube 13 into a blood corpuscle component 15 and blood serum component 14 by centrifugation or another suitable method. If the blood was treated with an anticoagulant such as heparin, the blood serum component 14 will be plasma. Next, 2 $\mu$l of the blood corpuscle component 15 and 18 $\mu$l of a previously prepared solution 17 from container 16 are mixed in a test tube 19, and are prereacted together. This solution 17 consists of an anti-A serum dilution prepared by diluting standard anti-A serum (Orso Co.) to 1/30 with physiological saline. After the preliminary reaction, 5 $\mu$l of blood corpuscle suspension 18 are pipetted by means of pipette 20 into reaction zone 5 of reaction zone defining means 21. Where the distance between lower plate 2 and upper plate 4 is 80 $\mu$m, the distance between the two spacers 3 is 500 $\mu$m and the length of the long direction of reaction zone 5 is 250 $\mu$m, and a supporting base wherein the slope of the inclined surface is 45°, all the human red blood cells sediment in the lower part of the reaction zone in about 10 minutes. After pipetting blood corpuscle suspension 18, therefore, the reaction zone defining means 21 is set on supporting base 1, and the base is left in an incubator at 36° C. for about 10 minutes.

The distance between the upper and lower plates and the distance between the two spacers are closely related to the time required to sediment the particles, and more specifically, should both be small in order to complete the sedimentation of particles in a short time. If however the distance between the two spacers is too small, the area where the particle distribution pattern is formed becomes smaller, and therefore the error of measurement increases. It is moreover necessary that the length of the long direction of the reaction zone is such that small quantities of the sample do not dry out during the reaction, and such that the sample can spread by capillarity throughout the whole of the reaction zone.

After the reaction zone defining is complete, the reaction means 21 is transferred to the measurement area. The measurement area comprises a light source 23 and a microscope optical system 25 to observe the blood corpuscle distribution pattern magnified, and it also has a photo sensor 26 to image the magnified blood corpuscle distribution in the reaction zone. The occurrence or non-occurrence of an antigen-antibody reaction is determined by magnifying the reaction zone 5 by means of optical system 25, and observing the blood corpuscle distribution pattern. Alternatively instead of observing the pattern with the naked eye, the image obtained by photo sensor 26 may be analyzed by a computer to determine the occurrence or non-occurrence of the reaction.

If the observed blood corpuscle distribution has a pattern of the type shown in FIG. 2A, it indicates that there are A antigens on the surface of the blood corpuscles in the sample, and that the blood corpuscles have agglutinated due to anti-A antibodies If on the other hand the blood corpuscle distribution has a pattern of the type shown in FIG. 2B, it indicates that there are no antigens on the surface of the blood corpuscles in the sample, and that the cells moved freely down the sloping surface of the reaction kit.

The reactivity of the sample with respect to anti-B serum is measured in the same way, and from its measured reactivity with respect to anti-A serum and anti-B serum, the blood group of the sample can be determined. If the blood corpuscles in the sample showed an antigen-antibody reaction with respect to both anti-A serum and anti-B serum, the blood group of the sample is AB; if there was a reaction only with respect to anti-A serum, the blood group of the sample is A; if there was a reaction only with respect to anti-B serum, the blood group of the sample is B; while if there was no reaction to either serum, the blood group of the sample is O.

The determination of blood group, which previously required 60 minutes, can be accomplished in about 10 minutes using the reaction vessel kit of this invention.

EXAMPLE 2

Assay for Anti-HIV Antibody

We shall describe an assay for anti-HIV antibody using the reaction kit of FIGS. 1A–1C with reference to FIG. 8.

First, a sample of blood is separated into a blood corpuscle component 15 and blood serum component 14 by centrifugation or another suitable method. If the blood was treated with an anticoagulant such as heparin, the blood serum component 14 will be plasma. After separation, 2 $\mu$l of the supernatant blood serum component 14 and 25 $\mu$l of a previously prepared solution 17 are mixed in a test tube 19, and prereacted together. This solution 17 consists of sensitized particles diluted to 1.0 % (v/v) with physiological saline, organically synthesized peptides having an identical amino acid sequence to HIV antigen being coated on the surface of these sensitized particles. The sensitized particles may consist of synthetic particles of polystyrene or gelatin which have been modified chemically, animal red blood cells fixated by glutaraldehyde or the like, or similar particles. The antigen used to sensitize the particles may be an inactivated virus, or a recombinant protein produced by *Escherichia coil* or the like using gene manipulation techniques. When the preliminary reaction is complete, 5 $\mu$l of a suspension of the sensitized particles is pipetted to reaction zone 5 by means of pipette 20, and the reaction means 21 is set on supporting base 1, and the base is left in incubator at 25°–37° C. for 10 min.

After the reaction is complete, the distribution of particles which have sedimented in reaction zone 5 is observed using the same method as in Example 1. If the observed particle distribution gives a pattern of the type shown in FIG. 2A, it indicates that there are anti-HIV antibodies in the serum of the sample, and that the particles have agglutinated due to the anti-HIV antibodies. If on the other hand the particle distribution gives a pattern of the type shown in FIG. 2B, it indicates that there are no antibodies in the sample reacting to the surface antigens of the sensitized particles.

By varying the type of antigen coated on the particles, an assay may be carried out for viruses or bacteria other than HIV such as HTLV-1, HB or gonococcus. Further, using antibody-sensitized particles, an assay for antigen may be carried out for HBs, drugs or cancer markers. Further, if particles of several different colors are made to conjugate respectively with different antibodies or antigens, and for example a color CCD camera is used as photo sensor 26, assays for several antibodies or antigens may be carried out in one operation.

Using the reaction kit of this invention, an assay can be thus be carried out with high sensitivity in 1/6 of the time conventionally required. Moreover, the assay may be performed using less of the costly particle reagent than was previously required.

EXAMPLE

Direct Cross-match Test for ABO Group Using a Reaction Kit with Antibodies Previously coated Thereon Firstly, an antiserum against A antigens on the surface of blood corpuscles is coated in the reaction zone 5 of a reaction kit as shown in FIGS. 1A–1C using the method described below.

First, standard anti-A serum (Orso Co.) is diluted to 1/10 with 10 mM Tris-HCl buffer solution, pH 9, containing 0.15 M NaCl. 5 ul of the diluted solution is dropped to reaction zone 5 of lower plate 2. After dropping of the solution, the lower plate is incubated at 37° C. for 1 hour while maintaining humid conditions so that the solution does not dry out. The reaction zone 5 is then washed by dropping 10 mM phosphate buffer solution, pH 7.2, containing 0.15 M NaCl. After removing the wash solution by gently shaking lower plate 2, 10 ml of 10 mM phosphate buffer solution, pH 7.2 containing 3% (w/v) of bovine serum albumin and 0.15 M NaCl are dropped to reaction zone 5, and the lower plate is incubated at room temperature while maintaining humid conditions for 1 hour. By this procedure, the area of the reaction zone which adsorbs blood corpuscles non-specifically is blocked. After incubation, reaction zone 5 is again washed with 10 mM phosphate buffer solution, pH 7.2, containing 0.15 M NaCl. If the lower plate is to be kept for a long period, 0.02% (w/v) $NaN_3$ is added to the final wash solution, and the lower plate is kept at 4° C. after washing. Moreover, in addition to lower plate 2, upper plate 4 is also treated so that non-specific conjugation with blood corpuscles does not occur. This is done by leaving the upper plate at room temperature for 1 hour in 10 mM phosphate buffer solution, pH 7.2, containing 3% (w/v) bovine serum albumin and 0.15 M NaCl, and washing it with 10 mM phosphate buffer solution, pH 7.2, containing 0.15 M NaCl. If the upper plate is to be left for a long period, 0.02% (w/v) $NaN_3$ is added to the final wash solution, and the upper plate is kept at 4° C. as in the case of the lower plate. In addition to this lower plate 2 and upper plate 4, the reaction is assembled using two spacers 3 which are fixed by means of double-sided adhesive tape o adhesive.

We shall now describe, with reference to FIG. 8, the direct cross-match test for ABO group using a reaction kit wherein an antiserum has been coated. in the kit used there, the spacers are of thickness 80 $\mu$m, the distance between the two spacers is 0.5 mm and the length of the long direction of the reaction zone is 5 mm, and a supporting base has inclination angle of 45°.

First, a sample of blood is separated into a blood corpuscle component 15 and blood serum component 14 by centrifugation or another suitable method. If the blood was treated with an anticoagulant such as heparin, the blood serum component 14 will be plasma. Next, 2 $\mu$l of the sedimented blood corpuscle component 15 and 98 $\mu$l of a solution 17 are mixed in a test tube 19 to prepare a 2% blood corpuscle suspension 18. In this case, solution 17 is physiological saline. This blood corpuscle suspension 18 is then introduced by means of a pipette 20 to reaction zone 5 wherein anti-A serum has been coated as described above. After pipetting, the reaction means 21 is set on supporting base 1 and incubated at about 36° C. for 10 min, care being taken not to shake the reaction zone. The pipetting may be performed after setting of the reaction means 21 on the supporting base 1.

Figure 7A:
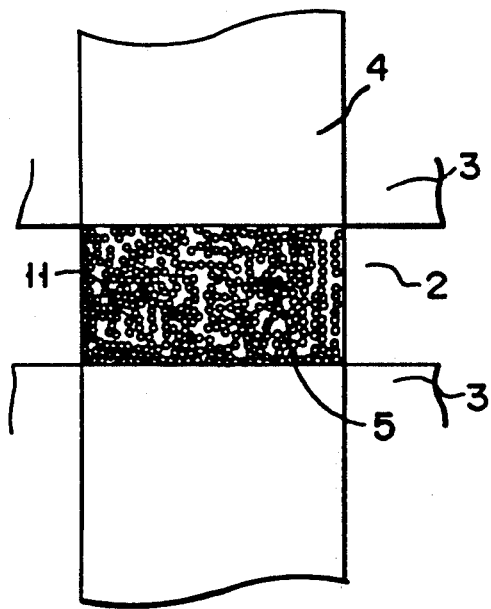
FIG. 7A shows a sediment particle distribution pattern obtained when there was an agglutination reaction in an agglutination test carried out using the reaction kit shown in FIGS. 1A–1C wherein antibodies have been coated in the reaction zone.
Figure 7B:
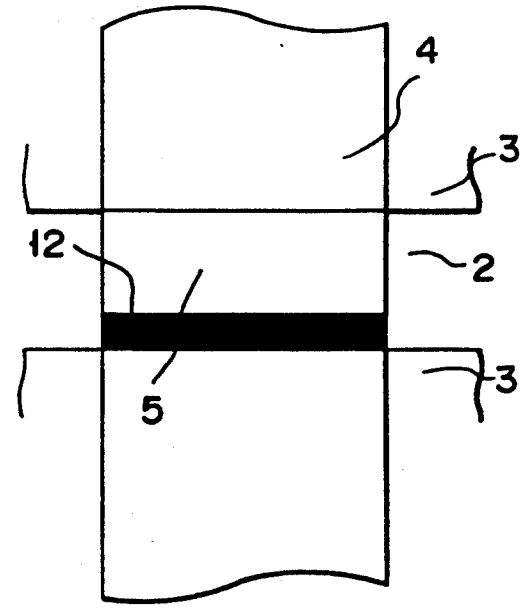
FIG. 7B shows a sediment particle distribution pattern obtained when there was no agglutination reaction in an agglutination test carried out using the reaction kit shown in FIGS. 1A–1C wherein antibodies have been coated in the reaction zone.

After the reaction is complete, the distribution pattern of particles sedimented in reaction zone 5 is observed as in Example 1. If there are A antigens on the surface of the blood corpuscles in the sample, the corpuscles conjugate with the anti-A serum that was coated in the reaction zone, and the blood corpuscles are uniformly distributed practically all over reaction zone 5. The corpuscle distribution which appears in this case therefore gives a pattern 11 of the type shown in FIG. 7A. If on the other hand there are no A antigens on the surface of the corpuscles in the sample, the blood corpuscles do not conjugate with the anti-A serum coated in the reaction and the corpuscles move freely down the inclined lower plate 2. In this case, therefore, the distribution of blood corpuscles gives a pattern 12 of the type shown in FIG. 7B. In this way, from the difference in the distribution pattern after reaction, it is possible to determine the presence or absence of A antigens on the surface of blood corpuscles in the sample. The presence or absence of B antigens on the surface of the blood corpuscles may be determined in the same way by measuring the reactivity of the sample with respect to anti-B serum.

From its measured reactivity with respect to anti-A serum and anti-B serum, the blood group of the sample can be determined. If the blood corpuscles in the sample showed an antigen-antibody reaction with respect to both anti-A serum and anti-B serum, the blood group of the sample is AB; if there was a reaction only with respect to anti-A serum, the blood group of the sample is A; if there was a reaction only with respect to anti-B serum, the blood group of the sample is B; while if there was no reaction to either serum, the blood group of the sample is O.

The determination of blood group, which previously required 60 minutes, can be accomplished in about 10 minutes using the reaction kit of this invention.

EXAMPLE 4

Figure 9:
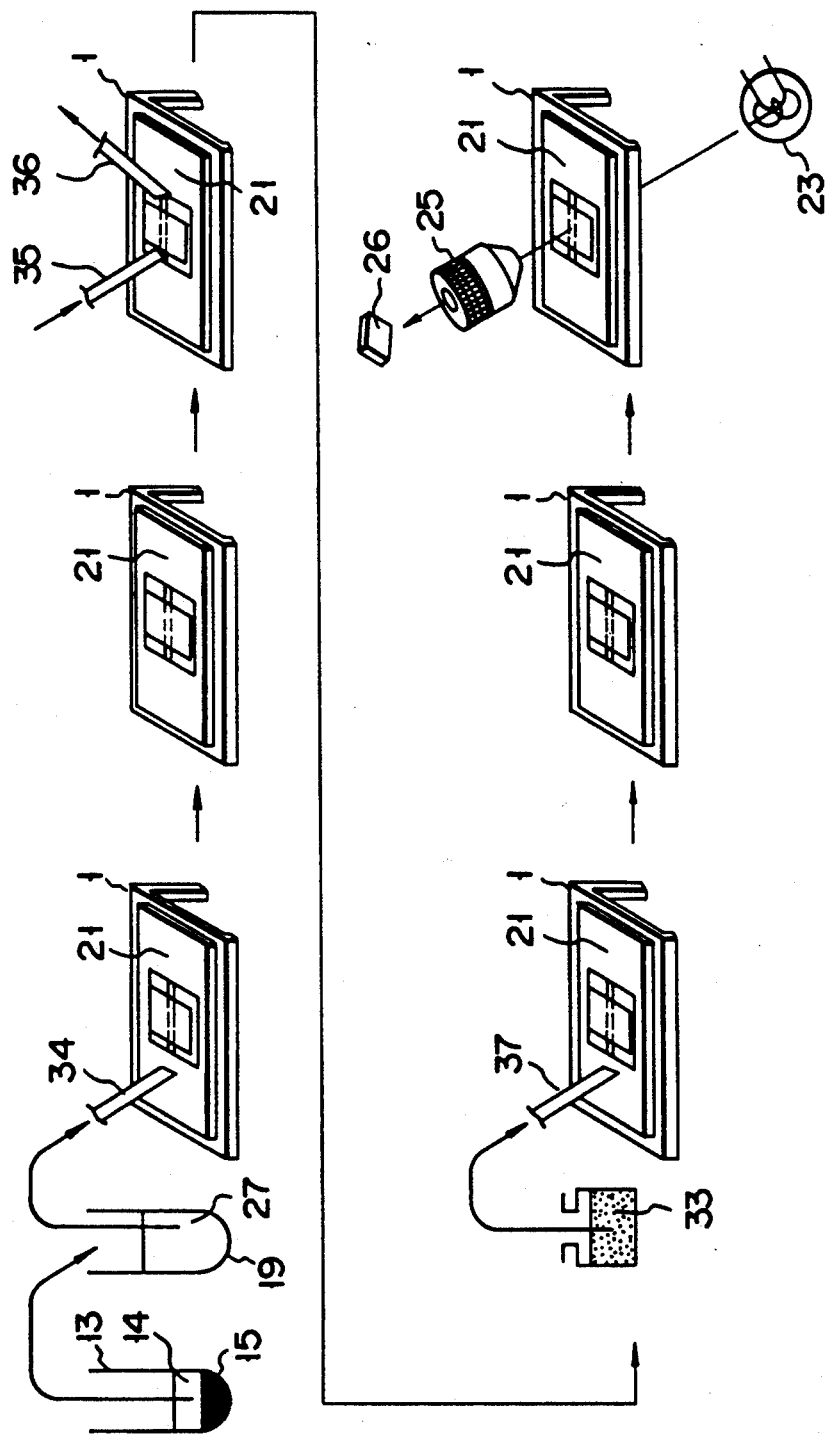
FIG. 9 is a view showing another process in an agglutination test using the reaction kit shown in FIGS. 1A–1C.

Assay for Anti-HIV Antibody Using a Reaction Kit with Antigens Previously Coated Thereon Assays for various antibodies can be carried out using a reaction kit wherein antigens have been coated instead of the anti-serum of Example 3. We shall describe an assay for anti-HIV antibody using such a method with reference to FIG. 9.

Firstly, using a similar method to that described in Example 3, HIV antigens are coated in the reaction zone 5. The HIV antigens coated in the reaction zone 5 may be chemically synthesized HIV virus surface antigens, HIV recombinant proteins produced by *Escherichia coil*, or the HIV virus itself.

Next, a sample of blood is separated in test tube 13 into a blood corpuscle component 15 and blood serum component 14 by centrifugation or another suitable method. If the blood was treated with an anticoagulant such as heparin, the blood serum component 14 will be plasma. 2 µl of the serum component obtained was removed in a test-tube 19, then 18 µl of physiological saline was added and mixed with it. 5 µl of this diluted serum solution 27 was pipetted by means of pipette 34 to a reaction zone 5 wherein HIV antigens had been coated. After pipetting, the reaction zone means was set on supporting base 1 and was incubated at 37° C. for 2 min. Following the reaction, physiological saline as wash solution was introduced by nozzle 35 into reaction zone 5 and waste liquid was aspirated simultaneously by nozzle 36 from the opposite side. By this procedure the reaction zone 5 can be washed, and the serum component which did not react with the antigen coated in reaction zone 5 can be washed out. It is desirable that wash solution remaining in reaction zone 5 is wiped off with filter paper, or eliminated by blowing in air from the nozzle.

Next, a particle reagent 33 to which goat antihuman antibodies had been coated, was introduced by means of nozzle 37 to the reaction zone, and the apparatus was incubated at 37° C. for 10 min. The anti-human antibodies used here may also be monoclonal antibodies derived from mouse or the like, or a substance such as protein A which binds to antibodies. Further, the particles on which the antibodies are coated may be red blood cells fixated by glutaraldehyde or the like, or synthetic particles such as polystyrene.

After the reaction is complete, the particle distribution pattern is observed by the same method as that of Example 1. If there are antibodies against for HIV in the serum of the sample, they conjugate with the HIV antigens coated in the reaction zone, and the particles to which anti-human antibodies have been coated conjugate with the antibodies which have conjugated with the antigens. The particle distribution is therefore a pattern of the type shown in FIG. 7A. If on the other hand there are no antibodies against HIV in the serum of the sample, the particles move freely down the inclined lower plate without causing an reaction. The particle distribution is therefore a pattern of the type shown in FIG. 7B.

Using this reaction kit, a high sensitivity assay can be performed in a much shorter time than the 60–120 min previously required.

By varying the type of antigen coated in the reaction zone, antibodies against viruses other than HIV such as HTLV-1 or HTLV-II or for bacteria may also be detected. Further, the antibody usually has 2–10 antigen binding sites. Particles to which the same antigen has been coated as the antigen coated in the reaction zone, may therefore also be used as particle reagent 33. Further, an assay for antigen may also be carried out by the "sandwich" method wherein antibodies are coated in both the reaction zone and on the particles.

What is claimed is:

1. A reaction kit for observation and detection of a particle pattern due to an agglutination reaction, comprising:
   reaction zone defining means for receiving a sample, said reaction zone defining means comprising:
   two plates arranged opposed to each other, at least one of said plates being transparent for visual detection therethrough of a particle pattern formed in said reaction zone; and
   spacers inserted between said two plates so as to maintain said two plates in spaced apart relation to each other, said reaction zone being defined in a space between said two plates and between said spacers; and a supporting base for supporting said reaction zone defining means, and including means for inclining said reaction zone defining means at a specified angle to thereby incline said reaction zone, such that one of said spacers forms a bottom portion of the inclined reaction zone;

a part of the space defined between said two plates and between said spacers serving as an opening through which a sample is introduced into said reaction zone, and wherein said opening is located in a position different from said spacer forming the bottom portion of the inclined reaction zone;

wherein a sample is aspirated into said reaction zone when the sample is applied to said reaction zone defining means.

2. The reaction kit of claim 1, wherein said two plates are both transparent.

3. The reaction kit of claim 1, wherein said reaction zone defining means and said supporting base are integrally formed as one unit.

4. The reaction kit of claim 1, wherein said reaction zone defining means includes a bottom surface facing said reaction zone, and further comprises a substance with specific bonding affinity to a sample, coated on at least said bottom surface of said reaction zone defining means.

5. The reaction kit of claim 1, wherein said spacers comprises two spaced apart spacers inserted between said two plates, said two spacers being spaced apart in a direction parallel to said two plates, and the reaction zone being defined in the space between said two spacers.

6. The reaction kit of claim 5, wherein said spacers are substantially flat plates.

7. The reaction kit of claim 5, wherein said reaction zone defining means defines said reaction zone having a substantially rectangular cross-section.

8. The reaction kit of claim 5, wherein said reaction zone defining means said reaction zone having a substantially rectangular cross-section.

9. The reaction kit of claim 1, wherein said spacers include surface means for defining an inlet port in flow communication with said reaction zone, said inlet port having a greater cross-sectional area than said reaction zone.

10. The reaction kit of claim 9, wherein said spacers comprise two spaced apart spacer plates inserted between said two plates, said two spacers being spaced apart in a direction parallel to said two plates, and the reaction zone being defined in the space between said two spacers, at least one of said spacer plates having an angled surface to define an inlet port in flow communication with said reaction zone, said inlet port having a greater cross-sectional area than said reaction zone.

11. The reaction kit of claim 1, wherein said reaction zone defining means further comprises:
means defining a trough adjacent said reaction zone.

12. The reaction kit of claim 11, wherein said reaction zone; and
means defining a trough adjacent the opposite openings of said reaction zone.

13. A method of determining a degree of particle agglutination by an agglutination reaction having the reaction kit according to claim 1, the method comprising:

preparing a particle suspension containing particles with specific bonding properties and a substance with specific bonding affinity to the particles;

introducing the particle suspension into a reaction zone of said reaction kit according to claim 1;

setting said reaction zone defining means on said supporting base, and leaving said reaction zone defining means, with the particle suspension therein, on said supporting base for a predetermined time; and observing the formation and degree of spread of a particle distribution pattern formed in a lower part of said reaction zone defined by said reaction zone defining means.

* * * * *